US006497574B1

(12) United States Patent
Miller (10) Patent No.: US 6,497,574 B1
(45) Date of Patent: Dec. 24, 2002

(54) MODIFIED TOOTH POSITIONING APPLIANCES AND METHODS AND SYSTEMS FOR THEIR MANUFACTURE

(75) Inventor: Ross J. Miller, Sunnyvale, CA (US)

(73) Assignee: Align Technology, Inc., Santa Clara, CA (US)

(*) Notice: Subject to any disclaimer, the term of this patent is extended or adjusted under 35 U.S.C. 154(b) by 157 days.

(21) Appl. No.: 09/658,340

(22) Filed: Sep. 8, 2000

(51) Int. Cl.[7] ............................................. A61C 11/00
(52) U.S. Cl. ......................................... 433/213; 433/24
(58) Field of Search ......................... 433/74, 213, 214, 433/34, 24

(56) References Cited

U.S. PATENT DOCUMENTS

| | | |
|---|---|---|
| 3,407,500 A | 10/1968 | Kesling |
| 3,600,808 A | 8/1971 | Reeve |
| 3,660,900 A | 5/1972 | Andrews |
| 3,683,502 A | 8/1972 | Wallshein |
| 3,860,803 A | 1/1975 | Levine |
| 3,922,786 A | 12/1975 | Lavin |
| 3,949,478 A * | 4/1976 | Schinhammer ............... 433/24 |
| 3,950,851 A | 4/1976 | Bergersen |
| 4,099,329 A * | 7/1978 | Hawthorne .................. 433/34 |
| 4,253,828 A | 3/1981 | Coles et al. |
| 4,324,546 A | 4/1982 | Heitlinger et al. |
| 4,324,547 A | 4/1982 | Arcan et al. |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,591,341 A | 5/1986 | Andrews |
| 4,609,349 A | 9/1986 | Cain |
| 4,664,626 A | 5/1987 | Kesling |
| 4,676,747 A | 6/1987 | Kesling |
| 4,755,139 A | 7/1988 | Abbatte et al. |
| 4,793,803 A | 12/1988 | Martz |

(List continued on next page.)

FOREIGN PATENT DOCUMENTS

| | | | |
|---|---|---|---|
| DE | 3900168 | * 10/1989 | ................. 433/213 |
| FR | 2369828 | 6/1978 | |
| WO | WO 94/10935 | 5/1994 | |
| WO | WO 98/32394 | 7/1998 | |
| WO | WO 98/58596 | 7/1998 | |

OTHER PUBLICATIONS

Andrews, "The Six Keys to Optimal Occlusion" *Straight Wire*, Chapter 3 pp. 13–24.

Biostar Opeation & Training Manual. Great Lakes Orthodontics, Ltd. 199 Fire Tower Drive, Tonawanda, New York. 14150–5890. 20 pages total.

(List continued on next page.)

*Primary Examiner*—Carl E. O'Connor
(74) *Attorney, Agent, or Firm*—Townsend and Townsend and Crew LLP; Bao Tran (57) ABSTRACT

The present invention provides improved devices, systems and methods for producing dental molds, each having portions representing a patient's oral soft tissue and a desired tooth configuration. These molds are designed for use in the fabrication of appliances used in orthodontic treatment, particularly, elastic repositioning appliances. However, they may also be used in the fabrication of traditional appliances, such as retainers and positioners, used, for example in the final or finishing stages of an otherwise conventional treatment. The dental molds are comprised of a mold or relief of the patient's soft tissue, such as a palate, facial gingival tissue and/or lingual gingival tissue, and a separate or separable mold or relief of the patient's dental arch having teeth in a desired tooth configuration. Since, the tooth configuration will change as a patient progresses through orthodontic treatment, the relief of the dental arch will be fabricated separately from the relief of the oral soft tissue. Typically, the dental arch relief will be fabricated using rapid prototyping methods. The soft tissue relief may also be fabricated using rapid prototyping, however it may also be fabricated using traditional mold making methods, i.e., casting with plaster or other mold making materials. In either case, the resulting dental mold with be comprised of a "split-mold" having fixedly or removably joined arch and soft tissue reliefs.

33 Claims, 5 Drawing Sheets

U.S. PATENT DOCUMENTS

| | | |
|---|---|---|
| 4,798,534 A | 1/1989 | Breads |
| 4,836,778 A | 6/1989 | Baumrind et al. |
| 4,837,732 A | 6/1989 | Brandestini et al. |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,936,862 A | 6/1990 | Walker et al. |
| 4,941,826 A | 7/1990 | Loran et al. |
| 4,983,334 A | 1/1991 | Adell |
| 5,011,405 A | 4/1991 | Lemchen |
| 5,017,133 A | 5/1991 | Miura |
| 5,035,613 A | 7/1991 | Breads et al. |
| 5,055,039 A | 10/1991 | Abatte et al. |
| 5,059,118 A | 10/1991 | Breads et al. |
| 5,100,316 A | 3/1992 | Wildman |
| 5,125,832 A | 6/1992 | Kesling |
| 5,139,419 A | 8/1992 | Andreiko et al. |
| 5,145,364 A | 9/1992 | Martz et al. |
| 5,186,623 A | 2/1993 | Breads et al. |
| 5,273,429 A | 12/1993 | Rekow et al. |
| 5,338,198 A | 8/1994 | Wu et al. |
| 5,340,309 A | 8/1994 | Robertson |
| 5,342,202 A | 8/1994 | Deshayes |
| 5,367,478 A | 11/1994 | Hattori |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,587,912 A | 12/1996 | Anderson et al. |
| 5,605,459 A | 2/1997 | Kuroda et al. |
| 5,607,305 A | 3/1997 | Andersson et al. |
| 5,645,420 A | 7/1997 | Bergersen |
| 5,645,421 A | 7/1997 | Slootsky |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,800,174 A | 9/1998 | Andersson |
| 5,866,058 A | 2/1999 | Batchelder et al. |
| 5,879,158 A | 3/1999 | Doyle et al. |
| 5,880,961 A | 3/1999 | Crump |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chisti et al. |
| 6,044,309 A | 3/2000 | Honda |
| 6,049,743 A | 4/2000 | Baba |
| 6,123,544 A | 9/2000 | Cleary |
| 6,183,248 B1 | 2/2001 | Chisti et al. |
| 6,190,165 B1 | 2/2001 | Andreiko et al. |
| 6,217,334 B1 | 4/2001 | Hultgren |
| 6,227,851 B1 * | 5/2001 | Chishti et al. ............ 433/74 |

OTHER PUBLICATIONS

Chiappone, "Constructing the gnathologic setup and positioner" *J. Clin. Orthod.* (1980) 14:121–133.

Cottingham, "Gnathologic clear plastic positioner" *Am. J. Orthod.* (1969) 55:23–31.

Cureton, "Correcting malaligned mandibular incisors with removable retainers" *J. Clin. Orthod.* (1996) 30:390–395.

Dent–X posted at http://www.dent–x.com/DentSim.htm Sep. 24, 1998, 6 pages total.

Elsasser, "Some observations of the history and uses of the Kesling positioner" *Am. J. Orthod.* (1950) 36:368–374.

Kamada et al., "Case reports on tooth positioners using LTV vinyl silicone rubber" *J. Nihon University School of Dentistry* (1984) 26(1):11–29.

Kamada et al., "Construction of tooth positioners with LTV vinyl silicone rubber and some case reports" *J. Nihon University School of Dentistry* (1982) 24(1):1–27.

Kesling, "Coordinating the predetermined pattern and tooth positioner with conventional treatment" *Am. J. Orthod. Oral. Surg.* (1946) 32:285–293.

Kesling, "The philosophy of the tooth positioning appliance" *Am. J. Orthod. Oral. Surg.* (1945) 31(6):297–304.

Kleemann et al., "The speed positioner" *J. Clin. Orthod.* (1996) 30:673–680.

Kunii et al., "Articulation Simulation for an Intelligent Dental Care System" *Displays* (1994) 15:181–188.

Kuroda et al., "Three–dimensional dental cast analyzing system using laser scanning" *Am. J. Orthod. Deftofac. Orthop.* (1996) 110:365–369.

Nahoum et al., "The vacuum formed dental contour appliance" *The New York State Dental Journal* (1964) 30(9):385–390.

*Nippon Dental Review* "New orthodontic device–dynamic positioner (D.P.)–I. Approach to the proposal of D.P. and transparent silicone rubber" (1980) 452:61–74.

*Nippon Dental Review* "New orthodontic device–dynamic positioner (D.P.)–II. Practical application and constructon of D.P." (1980) 454:107–130.

*Nippon Dental Review* "New orthodontic device–dynamic positioner (D.P.)–III. Case reports of reversed occlusion" 1980) 457:146–164.

*Nippon Dental Review* "New orthodontic device–dynamic positioner (D.P.)–Case reports of reversed occlusion" (1980) 458:112–129.

Nishiyama et al., "A new construction of tooth repositioner by LTV vinyl silicone rubber" *J. Nihon University School of Dentistry* (1977) 19(2):93–102.

Cardinal Industrial Finishes, Powder Coatings information posted at http:www.cardinalpaint.com on Aug. 25, 2000, 2 pages total.

Proffit et al, "Contemporary Orthodontics" Second Edition, Chapter 15, pp. 470–533.

*Raintree Essix™ & Materials, Inc.,* Raintree Essix™ Technical Magazine Table of Contents and Essix™ Applications, http://www.essix.com/magazine/default.html (Aug. 13, 1997) 7 pages total.

Richmond et al., "The development of the PAR Index (Peer Assessment Rating): reliability and validity" *European Journal of Orthodontics* (1992) 14:125–139.

Schroeder et al., Eds. *The Visual Toolkit,* Prentice Hall PTR, New Jersey (1998) Chapters 6, 8, and 9 (pp. 153–210, 309–354, and 355–428, respectively).

Shilliday, "Minimizing finishing problems with the mini–positioner" *Am. J. Orthod.* (1971) 59:596–599.

Warunek et al., "Clinical use of silicone elastomer applicances" *JCO* (1989) XXIII(10):694–700.

Warunek et al., "Physical and mechanical properties of elastomers in orthodontic positioners" *Am. J. Orthod. Dentofac. Orthop.* (1989) 95:388–400.

Wells, "Application of the positioner appliance in orthodontic treatment" *Am. J. Orthodont.* (1970) 58:351–366.

* cited by examiner

MODIFIED TOOTH POSITIONING APPLIANCES AND METHODS AND SYSTEMS FOR THEIR MANUFACTURE

BACKGROUND OF THE INVENTION

The present invention is related generally to the field of orthodontics. Particularly, the present invention is related to methods, systems and devices involving split dental molds. More particularly, the present invention involves dental molds having tooth portions and oral soft tissue portions of different types.

Traditional methods of dental mold making are well known, such as those described in Graber, *Orthodontics: Principle and Practice*, Second Edition, Saunders, Philadelphia, 1969, pp. 401–415. Typically, these methods involve forming an impression of the patent's dentition using a suitable impression material, such as alginate or polyvinylsiloxane (PVS). Impressions of the upper jaw typically include the teeth, the palate and gingival tissue surrounding the teeth on the facial and lingual surfaces. Impressions of the lower jaw typically include the teeth and gingival tissue surrounding the teeth on the facial and lingual surfaces. Plaster is then poured into the impression to form a relief of the dental features. The relief is a permanent, three-dimensional mold of the dentition and oral tissues.

Improved methods of mold making include rapid prototyping. Rapid prototyping is a technology which has developed in the last decade. Through the use of modern solid modeling CAD packages, combined with laser systems and new materials, solid parts may now be generated directly from a computer model. Examples of this technology include stereolithography (SLA), laminate object manufacturing (LOM), and fused deposition modeling (FDM), to name a few.

Stereolithography is a method that employs an ultraviolet laser to cure a thin layer of liquid plastic into a solid. The process operates by taking a thin layer of the light-sensitive liquid plastic and passing the laser beam over the points where the part is solid. Once a pass is completed, another layer of the liquid is added to the existing part, and the process repeats until the full part height is achieved. SLA parts are extremely accurate, and tend to have excellent surface finishes. A variety of SLA materials are available for different purposes, including waxes, plastics, and flexible elastomers.

Laminate object manufacturing builds a part by taking individual sheets of paper that have a layer of glue on one side and building up successive sections of a part. As each layer is laid down, a laser beam passes over the edges of the part, detailing the part and separating the part from the excess material. In addition, the laser beam creates a grid throughout the excess material. After the final sheet is laid down, the part may be separated from the excess material by removing cubes of the grid in a systematic fashion. LOM parts are accurate, and very easy to sand and paint. LOM parts also have different strengths in different directions due to the paper layers.

Fused deposition modeling is a process that most closely resembles a miniature glue gun. In fused deposition modeling, a heat softening and curing plastic is melted in a small nozzle which puts down a very fine bead wherever the solid part is supposed to be. FDM parts have a rougher surface finish than an SLA part, but typically are stronger and more durable. In all cases, parts created by rapid prototyping methods are generated relatively quickly and are accurate to a few thousandths of an inch.

Producing a dental mold with rapid prototyping methods requires the use of a computerized model or digital data set representing the dental geometry and tooth configuration. The model is used to guide the mold making process to produce a replica or relief of the computerized model. The resulting relief is a three-dimensional mold of the dentition. This method of making dental molds is particularly applicable to situations in which multiple molds are needed to be produced. In this case, one computerized model may be used to make a number of molds in an automated fashion. In addition, this method is applicable to situations in which a mold of a tooth arrangement which differs from the patient's current tooth arrangement is needed to be produced or molds of multiple tooth arrangements which differ from each other and the patient need to be produced. In either case, the computerized model of the patient's teeth may be manipulated to portray each new tooth arrangement and a mold may be produced to reflect each successive arrangement. This may be repeated any number of times to derive a number of molds with differing tooth arrangements. Such techniques may speed production time and reduce costs by eliminating the need for repeated casting and artistic resetting of teeth in traditional mold manufacturing.

Series of dental molds, such as those described above, may be used in the generation of elastic repositioning appliances for a new type of orthodontic treatment being developed by Align Technology, Inc., Santa Clara, Calif., assignee of the present application. Such appliances are generated by thermoforming a thin sheet of elastic material over a mold of a desired tooth arrangement to form a shell. The shell of the desired tooth arrangement generally conforms to a patient's teeth but is slightly out of alignment with the initial tooth configuration. Placement of the elastic positioner over the teeth applies controlled forces in specific locations to gradually move the teeth into the desired configuration. Repetition of this process with successive appliances comprising new configurations eventually moves the teeth through a series of intermediate configurations to a final desired configuration. A full description of an exemplary elastic polymeric positioning appliance is described in U.S. Pat. No. 5,975,893, and in published PCT application WO 98/58596 which designates the United States and which is assigned to the assignee of the present invention. Both documents are incorporated by reference for all purposes.

To carry out such orthodontic treatment, a series of computer models or digital data sets will be generated, stored and utilized to fabricate a series of representative dental molds. Typically, only the digital information related to the tooth arrangement will be stored due to cost and space limitations. However, to form a properly fitting elastic repositioning appliance or other dental appliance, it will at times be necessary to include in the mold a patient's oral soft tissue, such as a palate, facial gingival tissue and/or lingual gingival tissue. This may be the case when adding accessories to a basic elastic repositioning shell, such as palatal bars, lingual flanges, lingual pads, buccal shields, buccinator bows or wire shields, a full description of which is described in U.S. Provisional Patent Application No. 60/199649, filed Apr. 25, 2000, and the full disclosure is hereby incorporated by reference for all purposes. These accessories may contact or interact with portions of the soft tissue requiring a mold of such tissues to properly position the accessory in or on the appliance. In addition, this may be the case when producing traditional orthodontic retainers and positioners. Traditional appliances may be used as part of an orthodontic treatment plan utilizing elastic repositioning appliances, particularly in the final stages of treatment. During such stages, for example, any residual intrusion of the teeth due to the presence of elastic appliances may be corrected with the use of a traditional retainer. Such retainers typically comprise a polymeric replica of the palate or portions of the gingiva which support metal wires which wrap around the perimeter of the teeth.

Generating dental molds including both the tooth arrangement and the geometry of the oral soft tissue of a patient for each stage of treatment throughout orthodontic treatment is, however, expensive, due to cost of materials, fabrication time and space required for storage of digital information. Likewise, generating such a mold during treatment as necessary is also expensive due to 1) the added space required to store the additional digital information of the oral soft tissue, and 2) the time and labor required to manipulate the digital information to join a given tooth arrangement with an oral soft tissue geometry each time a mold is desired to be produced.

Therefore, improved devices, systems and methods are desired to design and fabricate dental molds suitable for the production of elastic repositioning appliances and other dental appliances which require structure corresponding to a patient's oral soft tissue. Such dental molds should provide an oral soft tissue relief or mold replicating the oral soft tissues of the patient and a relief of the desired tooth configuration, whether the configuration be the patient's current tooth configuration or a new tooth configuration desired in orthodontic treatment. Such dental molds should be economical, and in particular should reduce the cost of materials, fabrication time and labor, and space required for storage of digital information. At least some of these objectives will be met by the present invention described hereinafter.

SUMMARY OF THE INVENTION

The present invention provides improved devices, systems and methods for producing dental molds, each having portions representing a patient's oral soft tissue and a desired tooth configuration. These molds are designed for use in the fabrication of appliances used in orthodontic treatment, particularly, elastic repositioning appliances. However, they may also be used in the fabrication of traditional appliances, such as retainers and positioners, used, for example in the final or finishing stages of an otherwise conventional treatment. The dental molds are comprised of a mold or relief of the patient's soft tissue, such as a palate, facial gingival tissue and/or lingual gingival tissue, and a separate or separable mold or relief of the patient's dental arch having teeth in a desired tooth configuration. Since, the tooth configuration will change as a patient progresses through orthodontic treatment, the relief of the dental arch will be fabricated separately from the relief of the oral soft tissue. Typically, the dental arch relief will be fabricated using rapid prototyping methods. The soft tissue relief may also be fabricated using rapid prototyping, however it may also be fabricated using traditional mold making methods, i.e., casting with plaster or other mold making materials. In either case, the resulting dental mold with be comprised of a "split-mold" having fixedly or removably joined arch and soft tissue reliefs.

When a patient is treated with elastic repositioning appliances, a series of such appliances are produced to gradually reposition the patient's teeth from an initial tooth configuration, through a series of intermediate tooth configurations, to a final or other targeted tooth configuration. To accomplish this, the patient's initial tooth arrangement and shape of the patient's dental arch are represented by a digital data set in a computerized model. The data set is then manipulated to reflect progressive tooth arrangements. For each arrangement, the data is used to guide computerized model fabrication systems, or rapid prototyping systems, to create a corresponding three-dimensional mold or relief. As described above, such systems may include stereolithography (SLA), laminate object manufacturing (LOM), and fused deposition modeling (FDM), to name a few. Due to the methodology of rapid prototyping systems, the resulting relief is typically comprised of fused layers of material, such as wax, plastic, flexible elastomers or paper.

At a given point in treatment, it may be necessary to produce an appliance which requires a mold having the oral soft tissue features of the patient. Since the majority of the soft tissue areas remain unchanged throughout orthodontic treatment, it is not necessary to use computerized models or rapid prototyping methods to generate a relief of the patient's soft tissue features. One may simply rely on the oral features of the patient prior to treatment or at the present time and traditional mold making methods using plaster casting, for example. This may eliminate the need to create and store a digital data set representing the soft tissue and, consequently, the added time and labor to manipulate the data sets to join the soft tissue with the dental arch in the computerized model. The resulting split or composite mold will then usually be comprised of a plaster relief of the patient's oral soft tissue and a fused layered relief of the patient's dental arch having a tooth arrangement reflecting a future stage in the orthodontic treatment protocol. The split mold may then be used to produce the desired appliance.

Split molds of the present invention may be comprised of a number of designs and may be fabricated using a number of methods. In a first aspect of the present invention, a split mold of an upper or lower jaw of a patient may be comprised of a dental arch relief and an oral soft tissue relief, formed separately from the dental arch relief, wherein the two reliefs are fixedly joined together to anatomically resemble the jaw of the patient. This may be achieved by a number of methods. In an exemplary method, an impression or other cavity mold of the patient's jaw is produced by traditional methods, such as pressing a dental molding material against the dental features to form depressions or contours corresponding to the teeth and oral features. An SLA model of the desired tooth arrangement (without the majority of the soft tissue features) is also generated to provide the dental arch relief. However, it may be appreciated that the dental arch relief may be fabricated by any known method. The dental arch relief is then positioned in the impression so that contours of the arch relief generally correspond to corresponding contours of the impression or cavity mold. Since the arch relief will likely resemble a future tooth arrangement, the contours of the arch relief may not exactly fit the contours of the impression. However, the differences may be overcome by the flexibility of the impression. With the dental arch relief inserted, the exposed remainder of the impression represents the soft tissue. A mold of the soft tissue may be produced by at least partially filling the remainder of the impression with molding material. Preferred molding materials include, but are not limited to, plaster, urethane, silicone, epoxy and wax. The molding material will flow to fill in exposed areas around the tooth members and will form a relief of the soft tissue. After the material has cured, the fixedly joined reliefs may be removed from the impression. The resulting split-mold may then be used to produce a dental appliance requiring the presence of teeth and soft tissue features.

In a second aspect of the present invention, a split or composite mold of an upper or lower jaw of a patient may be comprised of a dental arch relief and an oral soft tissue relief, formed separately from the dental arch relief, wherein the two reliefs are separably or removably joined together to anatomically resemble the jaw of the patient. In a preferred embodiment, the oral soft tissue relief may be comprised of a portion or portions of the patient's gingival anatomy with vacant space(s) in the area of the dental arch. For example, the oral soft tissue relief may be comprised of a mold of a palate and facial gingival tissue wherein a vacant arch shaped "cutout" exists between the palate and the facial gingiva. A dental arch relief having a first tooth configuration may then be inserted into the arch shaped cutout to fill the vacant space. In particular, the dental arch relief will have a bottom or base which is configured to mate with the cutout in the palate and facial mold, and the present invention includes systems which comprise a plurality of dental arch reliefs (usually having different tooth arrangements) which may be interchangeably mounted into the palate and facial mold. The result is a corporate structure which anatomically resembles the jaw of the patient having a first tooth configuration. The dental arch relief may then be removed and a different dental arch relief having a second tooth configuration may be inserted. The result would be a corporate structure which anatomically resembles the jaw of the patient having the second tooth configuration. This may be repeated with any number of dental arch reliefs. Thus, the soft tissue relief may remain constant or act as a "universal" soft tissue mold, while the dental arch reliefs may be interchangeable to represent different configurations. It may be appreciated that the soft tissue relief may simply comprise a portion of the soft tissue, such as the palate or a lingual gingival surface, which may join with the arch relief in at one or more specific locations. For example, the soft tissue relief may join or attach to the side of the arch relief so that the arch relief is not specifically inserted into the soft tissue relief.

The dental arch relief is typically generated by rapid prototyping methods, as described above, such as SLA, LOM, and FDM. Consequently, the relief is often comprised of fused layers of waxes, plastics, flexible elastomers or paper. In addition, the relief may be painted or coated to provide desired surface characteristics. Although the dental arch relief is primarily comprised of tooth members, the gingiva surrounding the tooth members may also be represented. This may be necessary because the gingiva in contact with or near the tooth members may vary with the tooth configurations. Therefore, it may not be feasible to include this in the soft tissue relief and may be provided by the dental arch relief.

The oral soft tissue relief is typically generated by traditional mold making methods. This may involve forming an impression of the patient's jaw using a suitable impression material, such as alginate or polyvinylsiloxane (PVS). Usually, this will include both the teeth and the oral soft tissues to ensure complete coverage. Plaster or other material may be poured into the impression to form a relief of the dental features. Upon removal of the mold from the impression, the mold may then be modified for use. The mold may be cut or trimmed to isolate a desired portion of the oral soft tissue relief. For example, the dental arch may be removed from the mold, leaving the relief of the palate and facial gingival surfaces intact. In this case, the mold may appear as an oral soft tissue relief having an arch-shaped hole or vacant space in place of the teeth. Thus, a dental arch relief, described above, may be inserted through the arch-shaped hole and held in place. The result may be a split-mold which anatomically resembles the jaw of the patient and may be used to produce a properly fitting appliance.

Similarly, other portions of the mold may be removed leaving portions of the soft tissue relief intact. For example, the lingual gingival surfaces of a lower jaw mold may be cut and isolated for use. In this case, the gingival surfaces or soft tissue relief may be joined with a dental arch relief by placing them in close proximity, snapping them together, bonding them together or joining them by any suitable method. Again, the result may be a split-mold which anatomically resembles portions of the jaw of the patient and may be used to produce a properly fitting appliance. For some appliances, this may be accomplished by heating a thermoformable polymer material and applying vacuum or pressure to form the polymer to the mold. An accessory, such as a lingual pad, may be formed in the appliance which contacts or interacts with the patient's lingual gingival surfaces.

The oral soft tissue relief may also be generated by rapid prototyping methods, as described above, such as SLA, LOM, and FDM. In this case, a digital data set may be created representing the oral soft tissue. The data set may be used to guide the computerized model fabrication systems to create a corresponding three-dimensional mold or relief. Since the data set may be modified prior to model fabrication, the resulting oral soft tissue relief may be generated in a usable form. Otherwise, the relief may be modified by manual methods so isolate the desired portion of the relief. In any case, the oral soft tissue relief may then be joined with a dental arch relief by placing them in close proximity, snapping them together, bonding them together or joining them by any suitable method. Again, the result may be a split-mold which anatomically resembles portions of the jaw of the patient and may be used to produce a properly fitting appliance. Although the reliefs may be comprised of the same material generated by the same methods, the advantages of the split-mold design are still available. The dental arch relief having a first tooth configuration may be removed and a dental arch relief having a second tooth configuration may be joined to the oral soft tissue relief. And, this may be repeated with third, fourth, fifth, and more tooth configurations. In addition, the digital data set may be used only once to fabricate a "universal" oral soft tissue relief. This may eliminate time and labor associated with manipulating the data sets to join the dental arch and the gingival tissues in the computer model at various times throughout the treatment. In addition, the digital data set representing the oral soft tissue may be deleted once the oral soft tissue relief is fabricated. This may eliminate the need for additional storage space.

Other objects and advantages of the present invention will become apparent from the detailed description to follow, together with the accompanying drawings.

DESCRIPTION OF THE SPECIFIC EMBODIMENTS

Split molds of the present invention may be comprised of a number of designs and may be fabricated using a number of methods. As previously described, a split mold of an upper or lower jaw of a patient may be comprised of a dental arch relief and an oral soft tissue relief, formed separately from the dental arch relief. The reliefs may be fixedly or removably joined together to anatomically resemble the jaw of the patient.

Figure 1:
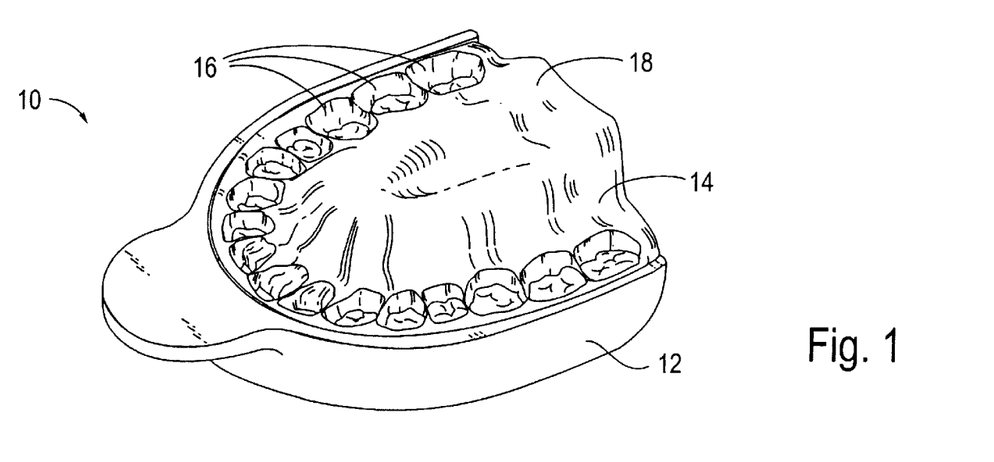
FIG. 1 is a perspective illustration of an dental impression made from a patient's jaw.
Figure 2:
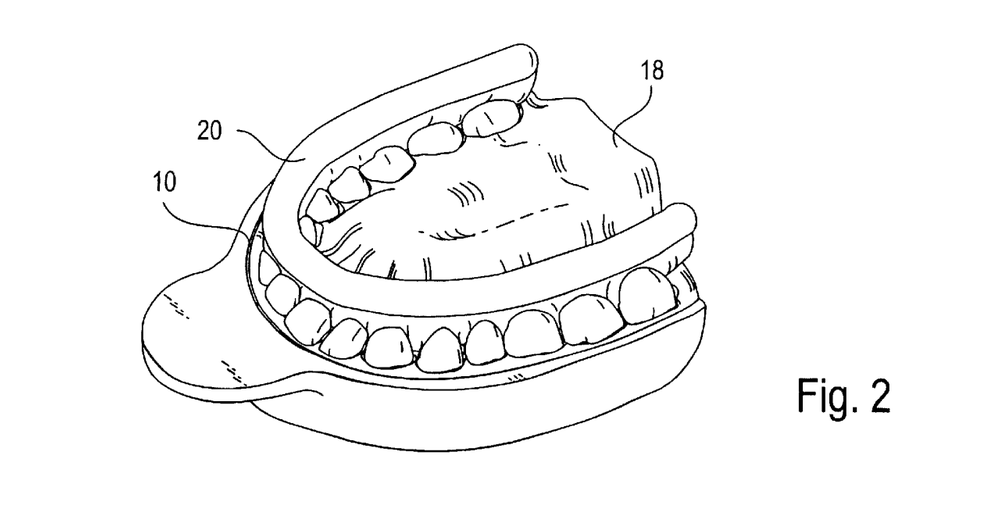
FIG. 2 illustrates the step of positioning a dental arch relief in the impression depicted in FIG. 1.
Figure 3:
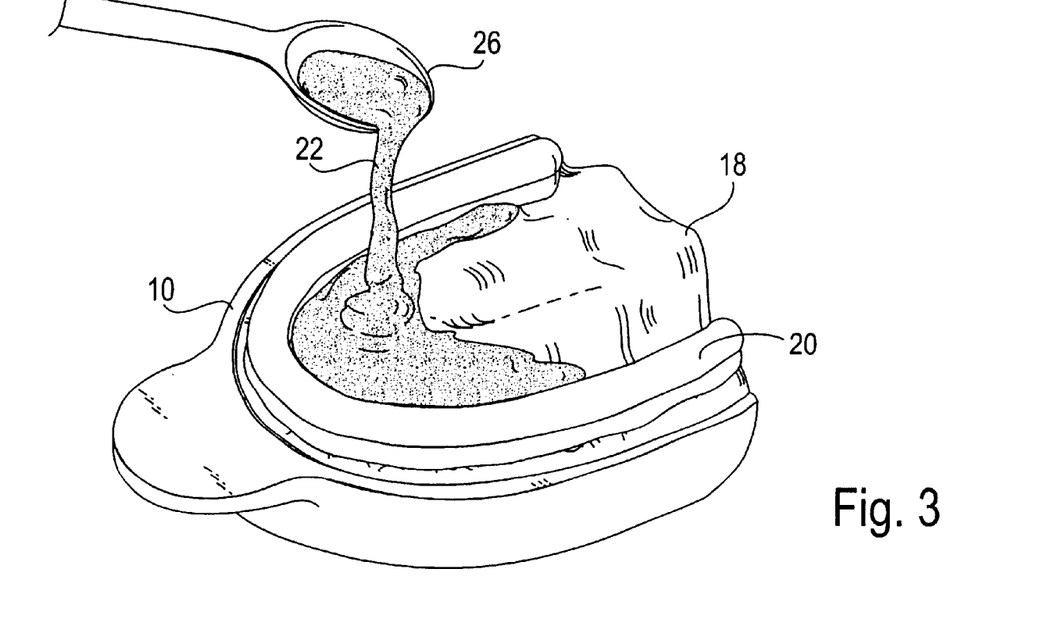
FIG. 3, illustrates the step of filling a remainder of the impression of FIG. 1 with a molding material.
Figure 4:
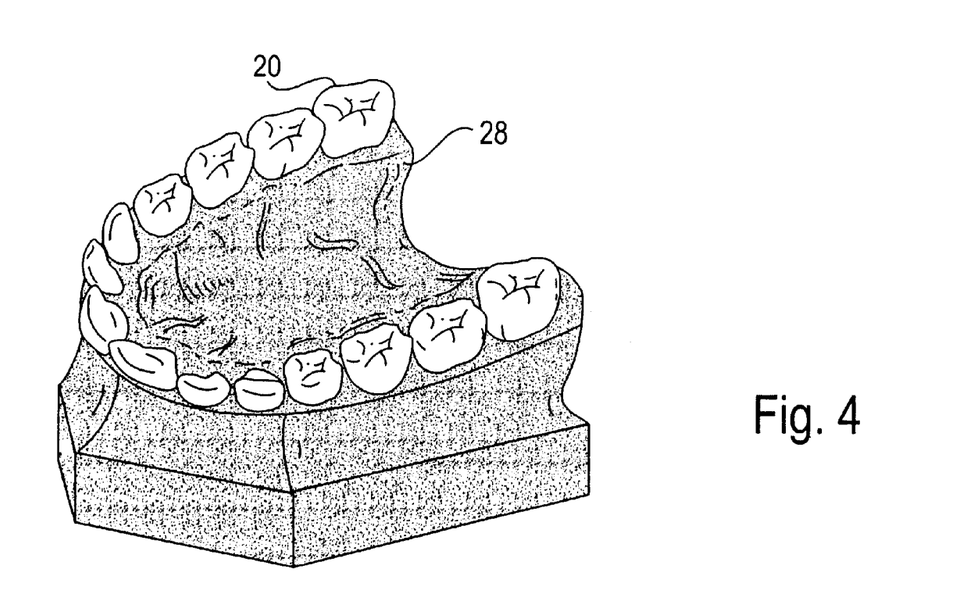
FIG. 4 is a perspective illustration of a split-mold formed by methods of the present invention illustrated in FIGS. 1–3.

In a first aspect of the present invention, the split mold may be produced wherein the dental arch relief and oral soft tissue relief are fixedly joined. Referring to FIG. 1, the a preferred method may begin by forming an impression 10 of the patient's jaw. A holder 12 may be filled with dental molding material 14, such as alginate, inserted in the patient's mouth and pressed against the patient's dental features. The resulting impression 10 may have depressions or contours in the material corresponding to the teeth 16 and oral features, such as the palate 18. As shown in FIG. 2, a dental arch relief 20, fabricated by any known method, particularly SLA, may then be positioned in the impression 10 so that contours of the arch relief generally correspond to contours of the impression. With the dental arch 20 inserted, the exposed remainder of the impression 10, such as the palate 18, represents the soft tissue. Referring to FIG. 3, the mold of the soft tissue may be produced by filling the remainder of the impression 10 with molding material 22. The molding material 22 is depicted flowing from a spoon 26 into the region of the palate 18. In this manner, the material 22 will flow around the dental arch relief 20 and will fill in exposed areas around the tooth members. After the material 22 has cured, the impression 20 may be removed. The result, as shown in FIG. 4, may be comprised of a dental arch relief 20 and an oral soft tissue relief 28 fixedly joined. In this case, the oral soft tissue relief 28 may comprise the entire surface area of the mold aside from the tooth members. This is possible due to the methodology of fabrication.

Figure 5A:
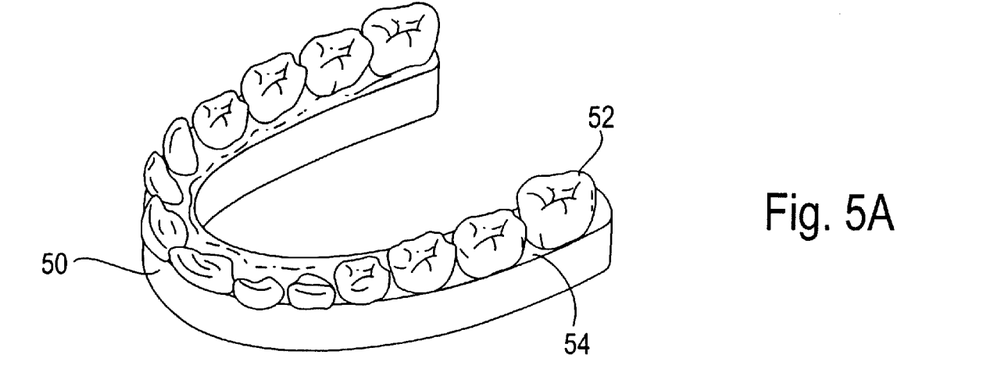
FIG. 5A depicts a dental arch relief of an upper jaw.
Figure 5B:
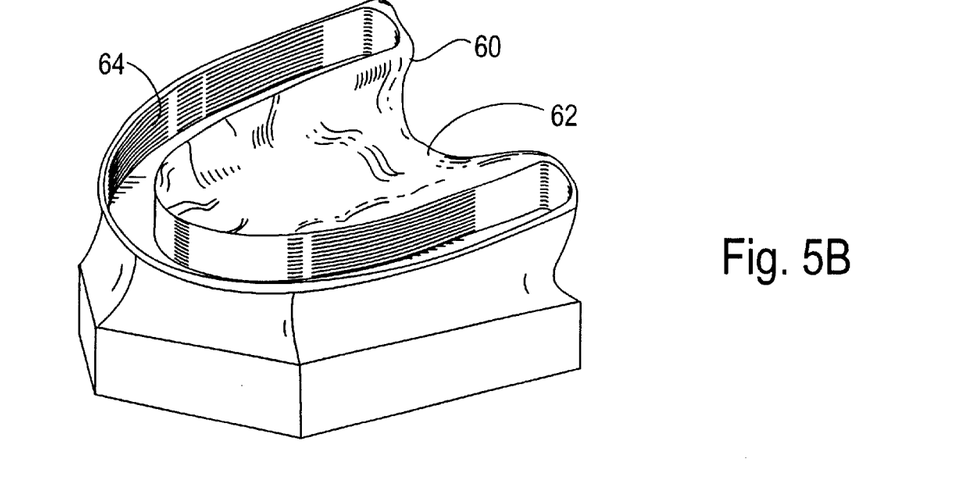
FIG. 5B depicts an oral soft tissue relief having a cutout in the area of the dental arch.
Figure 5C:
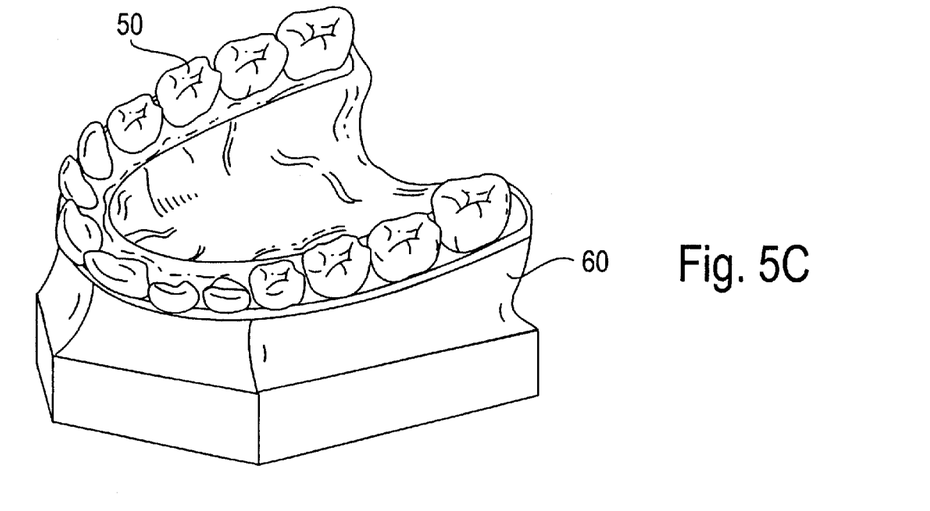
FIG. 5C is a perspective illustration of a split-mold formed by joining the reliefs depicted in FIGS. 5A–5B.

In a second aspect of the present invention, the split mold may be produced wherein the dental arch relief and oral soft tissue relief are removably joined. A preferred embodiment of such a system is illustrated in FIGS. 5A–C. FIG. 5A depicts a first dental arch relief 50 of an upper jaw having a first tooth configuration. In this case, the dental arch relief 50 may provide a mold of tooth members 52 and gingival tissue 54 surrounding the tooth members 52 along the arch. FIG. 5B depicts an oral soft tissue relief 60 of an upper jaw, including a palate 62. As shown, an arch-shaped cutout 64 or vacant space may exist surrounding the palate 62. The dental arch relief 50 may then be inserted into the cutout 64 to fill the vacant space. The resulting split-mold, shown in FIG. 5C, comprises a dental arch relief 50 and oral soft tissue relief 60 removably joined to anatomically resemble the upper jaw of the patient having the first tooth configuration. The arch relief 50 may then be removed and a second dental arch relief having a second tooth configuration, similar to the relief 50 depicted in FIG. 5A with a slightly differing tooth arrangement, may be inserted into the cutout 64. The resulting split-mold may anatomically resemble the upper jaw of the patient having the second tooth configuration. This may be repeated with any number of dental arch reliefs.

Figure 6A:
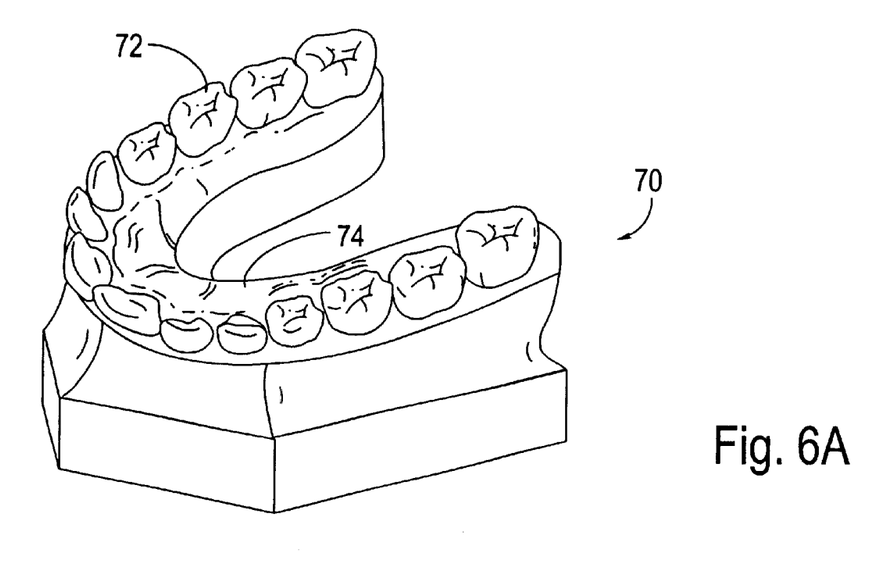
FIG. 6A depicts a mold of a lower jaw of a patient.
Figure 6B:
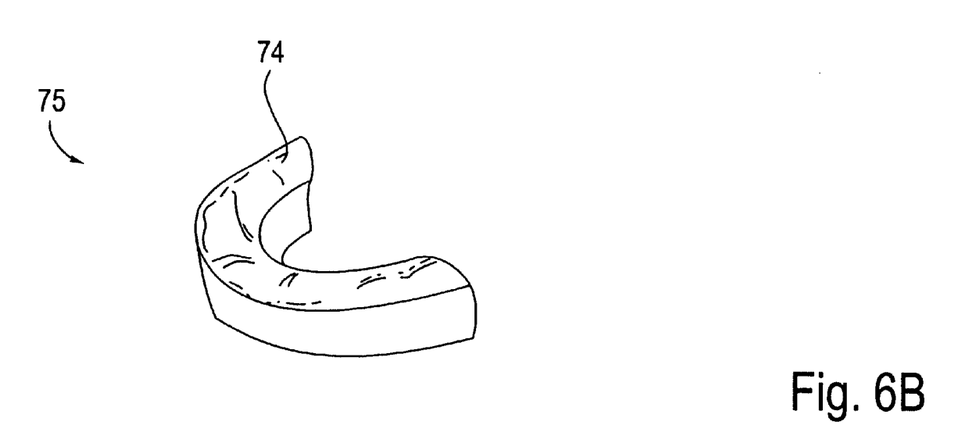
FIG. 6B depicts an oral soft tissue relief, representing the portions of the lingual gingival surfaces of the patient's lower jaw, which has been cut and removed from the mold depicted in FIG. 6A.

The above described system may be produced using a number of methods. In a preferred method, the oral soft tissue relief is generated by traditional mold making methods. This may involve forming an impression of the patient's jaw using a suitable impression material, such as alginate or polyvinylsiloxane (PVS). Plaster or other material may be poured into the impression to form a relief of the dental features. Upon removal from the impression, a three-dimensional mold results. An example of such a mold 70 of a lower jaw of a patient is depicted in FIG. 6A. As shown, the mold 70 may have features representing both tooth members 72 and lingual gingival tissue 74, for example. The mold 70 may be cut or trimmed to isolate the lingual gingival tissue 74. The result, depicted in FIG. 6B, is an oral soft tissue relief 75 of the lingual gingival tissue.

Figure 7:
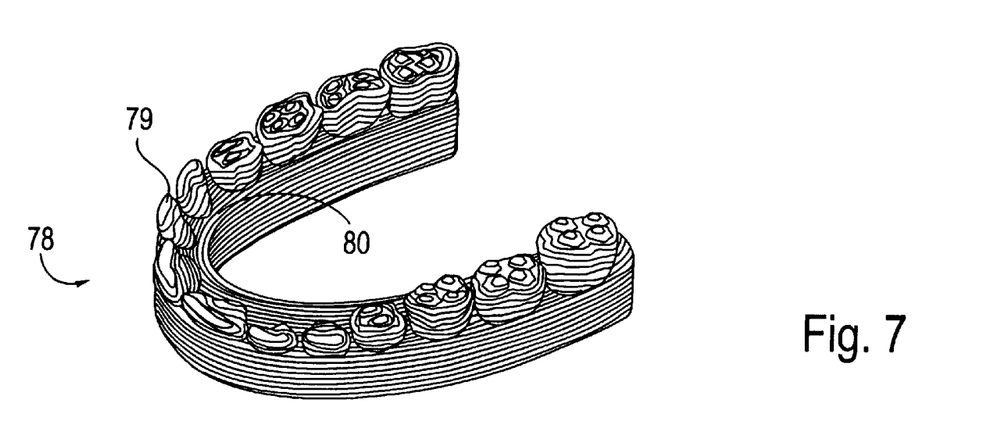
FIG. 7 depicts an dental arch relief of a lower jaw.
Figure 8:
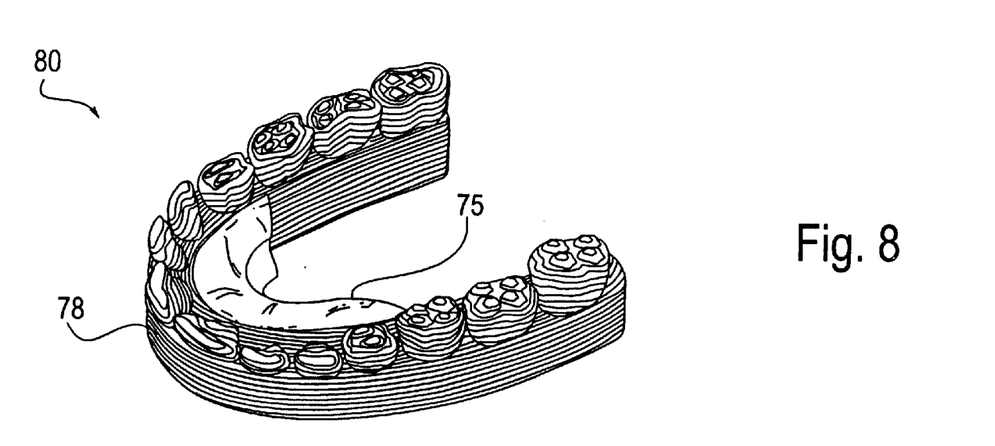
FIG. 8 Is a perspective illustration of a split-mold formed by methods of the present invention illustrated in FIGS. 6A, 6B, and 7.

A dental arch relief may be generated by any method, but will typically be generated by rapid prototyping methods, such as SLA, LOM, and FDM, to name a few. As used herein, "rapid prototyping" will refer to any computer-controlled method for directly fabricating the relief structure from a structuring material. SLA, LOM, and FDM, are presently the best known of such techniques, but other and future techniques will also be useful. In these cases, the dental arch relief is comprised of fused layers of waxes, plastics, flexible elastomers or paper. Such a dental arch relief 78 is depicted in FIG. 7 and represents a lower jaw having a first tooth configuration. Again, the dental arch relief 78 may provide a mold of tooth members 79 and gingival tissue 80 surrounding the tooth members 79 along the arch. Horizontal lines throughout the relief 78 illustrate such layers. Referring to FIG. 8, the dental arch relief 78 and the oral soft tissue relief 75 may be joined to form a split-mold 80 which resembles portions of the lower jaw of the patient. Such joining may be removable or fixed.

Removably joining the reliefs may involve a number of methods to hold the reliefs in place. For instance, the reliefs may be interlocking or snap together to form a joined mold. Or, the reliefs may be attached by any type of fastener, screw, bolt, hook, clasp, hoop-and-loop fasteners (e.g., those available under the tradename Velcro®), or similar device. Likewise, the reliefs may be removably bonded by tape, adhesive, or similar material. And finally, the reliefs may be press-fit and held by wedging or friction. It may be appreciated that a combination of any of these methods may be used or similar methods that may provide the same function. Further, it may be appreciated that the reliefs may be joined simply by placing the reliefs in close proximity to each other. A soft tissue relief may be positioned in a desired location near a portion or portions of the dental relief, and the reliefs may be used together in the production of a dental appliance. Also, any of the removably joined reliefs may become permanently joined or fixedly attached by the addition of a material, agent or device which will fixedly bond the relief materials, such as an adhesive.

The resulting split-mold resembles portions of the lower jaw of the patient and may be used to produce a properly fitting appliance. For some appliances, this may be accomplished by heating a thermoformable polymer material and applying vacuum or pressure to form the polymer to the mold. In this case, a lingual pad or similar accessory may be formed in the appliance which contacts or interacts with the patient's lingual gingival surfaces of the lower jaw.

In addition, the oral soft tissue relief 75 may be produced by any other method, including rapid prototyping methods. FIGS. 6A, 6B, 7 and 8 also illustrate such a method but may be further visualized by adding horizontal lines throughout the mold 70 and the oral soft tissue relief 75 to illustrate a layered material composition. As previously mentioned, the advantages of the split-mold design are still available when the reliefs are be comprised of the same material generated by the same methods. The dental arch relief having a first tooth configuration may be removed and a dental arch relief having a second tooth configuration may be joined to the oral soft tissue relief. And, this may be repeated with third, fourth, fifth, and more tooth configurations. In addition, the digital data set may be used only once to fabricate a "universal" oral soft tissue relief. This may eliminate time and labor associated with manipulating the data sets to join the dental arch and the gingival tissues in the computer model at various times throughout the treatment. In addition, the digital data set representing the oral soft tissue may be deleted once the oral soft tissue relief is fabricated. This may eliminate the need for additional storage space.

Although the foregoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A method of making a dental mold of a jaw of a patient comprising:
   providing a cavity mold of the jaw, wherein the jaw comprises a dental arch and oral soft tissue;
   providing a dental arch relief;
   positioning the dental arch relief in the cavity mold that contours of the arch relief generally fit into corresponding contours of the cavity mold; and
   at least partially filling the remainder of the cavity mold with a molding material so that the molding material forms the oral soft tissue relief.

2. A method of claim 1, wherein the dental arch comprises tooth members.

3. A method of claim 1, wherein the oral soft tissue comprises a palate, facial gingival surfaces, lingual gingival surfaces, and/or gingiva surrounding the tooth members.

4. A method of claim 1, wherein the arch relief comprises fused layers of waxes, plastics, flexible elastomers, or paper.

5. A method of claim 4, wherein providing a dental arch relief further comprises forming the arch relief by a rapid prototyping method.

6. A method of claim 5, wherein the rapid prototyping method is selected from the group consisting of stereolithography, laminate object manufacturing and fused deposition modeling.

7. A method of claim 1, wherein the molding material is selected from the group consisting of plaster, urethane, silicone, epoxy and wax.

8. A method for producing a series of dental molds representing a jaw of a patient, said method comprising:
   providing at least one oral soft tissue relief;
   joining a first dental arch relief to the oral soft tissue relief to produce a first dental mold; and
   joining a second dental arch relief to the same or a second oral soft tissue relief to produce a second dental mold.

9. A method as in claim 8, wherein providing comprises providing at least two oral soft tissue reliefs and wherein the first dental arch relief is joined to a first oral soft tissue relief and the second dental arch relief is joined to a second oral soft tissue relief.

10. A method as in claim 8, further comprising separating the first dental "arch" relief from the first dental mold and thereafter joining the second dental arch relief to the same oral soft tissue relief to form the second dental mold.

11. A method as in claim 8, wherein providing at least one oral soft tissue relief comprises:
    providing a cavity mold of the jaw, wherein the jaw comprises a dental arch and oral soft tissue;
    positioning a dental arch relief in the cavity mold so that contours of the arch relief generally fit into corresponding contours of the cavity mold at least partially filling the remainder of the cavity mold with a molding material so that the molding material forms the oral soft tissue relief.

12. A method as in claim 8, further comprising forming the first and second dental arches by a rapid prototyping method.

13. A method as in claim 12, wherein the rapid prototyping is selected from the group consisting of stereolithography (SLA), laminate object manufacturing (LOM), and fused deposition modeling (FDM).

14. A dental mold of a jaw of a patient comprising:
    a dental arch relief comprises a material selected for the group consisting of fused layers of waxes, plastics, flexible elastomers and paper; and
    an oral soft tissue relief formed separately from the dental arch relief,
    wherein the arch relief and the tissue relief are joined.

15. A dental mold of claim 14, wherein the dental arch comprises tooth members.

16. A dental mold of claim 14, wherein the oral soft tissue comprises at least one of a palate, a facial gingival tissue, and a lingual gingival tissue.

17. A dental mold of claim 14, wherein the arch relief and the tissue relief are separably joined.

18. A dental mold of claim 14, wherein the arch relief and the tissue relief are fixedly joined.

19. A dental mold of claim 14, wherein the oral soft tissue relief comprises a material selected for the group consisting of plaster, fused layers of waxes, plastics, flexible elastomers, and paper.

20. A system of modeling a jaw of a patient during tooth repositioning for orthodontic treatment, said system comprising:
    an oral soft tissue relief;
    a first dental arch relief having a first tooth configuration, wherein the first dental arch relief is removably joinable with the oral soft tissue relief so that together the first dental arch relief and tissue relief anatomically resemble the jaw of the patient having the first tooth configuration; and
    a second dental arch relief having a second tooth configuration which is different from the first tooth configuration, wherein the second dental arch relief is removably joinable with the oral soft tissue relief so that together the second dental arch and tissue relief anatomically resemble the jaw of the patient having the second tooth configuration.

21. A system as in claim 20, wherein the oral soft tissue comprises a palate, a facial gingival surface, and/or a lingual gingival surface.

22. A system as in claim 20, wherein the arch relief comprises fused layers of waxes, plastics, flexible elastomers, or paper.

23. A system as in claim 20, wherein the oral soft tissue comprises plaster, or fused layers of waxes, plastics, flexible elastomers, or paper.

24. A system of claim 20, further comprising a third dental arch relief having a third tooth configuration, wherein the third dental arch relief is removably joinable with the oral soft tissue relief so that together the third dental arch relief and the tissue relief anatomically resemble the jaw of the patient having the third tooth configuration.

25. A system of modeling a jaw of a patient during tooth repositioning for orthodontic treatment, said system comprising:

a first dental arch relief having a first tooth configuration and comprising fused layers of waxes, plastics, flexible elastomers, or paper; and an oral soft tissue relief, wherein the first dental arch relief is removably joinable with the oral soft tissue relief so that together the first dental arch relief and tissue relief anatomically resemble the jaw of the patient having the first tooth configuration.

26. A system as in claim 25, further comprising a second dental arch relief having a second tooth configuration which is different from the first tooth configuration, wherein the second dental arch relief is removably joinable with the oral soft tissue relief so that together the second dental arch and tissue relief anatomically resemble the jaw of the patient having the second tooth configuration.

27. A system as in claim 25, wherein the oral soft tissue comprises a palate, a facial gingival surface, and/or a lingual gingival surface.

28. A system as in claim 25, wherein the oral soft tissue comprises plaster, or fused layers of waxes, plastics, flexible elastomers, or paper.

29. A system of claim 25, further comprising a third dental arch relief having a third tooth configuration, wherein the third dental arch relief is removably joinable with the oral soft tissue relief so that together the third dental arch relief and the tissue relief anatomically resemble the jaw of the patient having the third tooth configuration.

30. A system of modeling a jaw of a patient during tooth repositioning for orthodontic treatment, said system comprising:

an oral soft tissue relief;

a first dental arch relief having a first tooth configuration, wherein the first dental arch relief is removably joinable with the oral soft tissue relief so that together the first dental arch relief and tissue relief anatomically resemble the jaw of the patient having the first tooth configuration;

a second dental arch relief having a second tooth configuration which is different from the first tooth configuration, wherein the second dental arch relief is removably joinable with the oral soft tissue relief so that together the second dental arch and tissue relief anatomically resemble the jaw of the patient having the second tooth configuration; and a third dental arch relief having a third tooth configuration, wherein the third dental arch relief is removably joinable with the oral soft tissue relief so that together the third dental arch relief and the tissue relief anatomically resemble the jaw of the patient having the third tooth configuration.

31. A system as in claim 30, wherein the oral soft tissue comprises a palate, a facial gingival surface, and/or a lingual gingival surface.

32. A system as in claim 30, wherein the arch relief comprises fused layers of waxes, plastics, flexible elastomers, or paper.

33. A system as in claim 30, wherein the oral soft tissue comprises plaster, or fused layers of waxes, plastics, flexible elastomers, or paper.

* * * * *